United States Patent [19]
Nishio et al.

[11] Patent Number: 5,381,194
[45] Date of Patent: Jan. 10, 1995

[54] APPARATUS FOR PHOTOGRAPHING A CORNEAL ENDOTHELIUM

[75] Inventors: Kouji Nishio; Akio Morimoto, both of Tokyo, Japan

[73] Assignee: Kabushiki Kaisha TOPCON, Tokyo, Japan

[21] Appl. No.: 13,800

[22] Filed: Feb. 5, 1993

[30] Foreign Application Priority Data

Feb. 7, 1992 [JP] Japan .................. 4-022447

[51] Int. Cl.⁶ .................. A61B 3/14; A61B 1/04; G06F 15/42
[52] U.S. Cl. .................. 351/208; 351/206; 351/211; 351/221; 354/62; 364/413.13
[58] Field of Search .............. 606/4; 128/745; 354/62; 364/413.13; 351/205, 206, 208, 211, 214, 216, 220, 221

[56] References Cited

U.S. PATENT DOCUMENTS

| | | | |
|---|---|---|---|
| 3,762,803 | 10/1973 | Papritz | 351/206 |
| 4,323,299 | 4/1982 | Roberts | 351/221 |
| 4,976,535 | 12/1990 | Reis | 351/219 |
| 5,098,426 | 3/1992 | Sklar et al. | 351/209 |
| 5,177,512 | 1/1993 | Abe et al. | 351/206 |

*Primary Examiner*—William L. Sikes
*Assistant Examiner*—David R. Parsons
*Attorney, Agent, or Firm*—Finnegan, Henderson, Farabow, Garrett & Dunner

[57] ABSTRACT

An apparatus for photographing a corneal endothelium of a patient's eye according to the invention includes an optical system for observing the anterior segment of the eye to align optical systems of the apparatus with the eye; an illumination optical system for projecting each illumination light emitted by a light source for observation and a light source for photography onto the cornea of the eye; an endothelium observing and photographing optical system for receiving reflected light from the corneal endothelium and observing and photographing it, the observing and photographing optical system including a reflected light receiving element for aligning the optical systems of the apparatus in the back and forth directions with the eye; display means for displaying images of the anterior segment and the corneal endothelium separately from each other; and image switching means for switching a displayed image from the anterior segment to the corneal endothelium and vice versa.

7 Claims, 25 Drawing Sheets

SECTIONING DIRECTION OF THE CORNEA

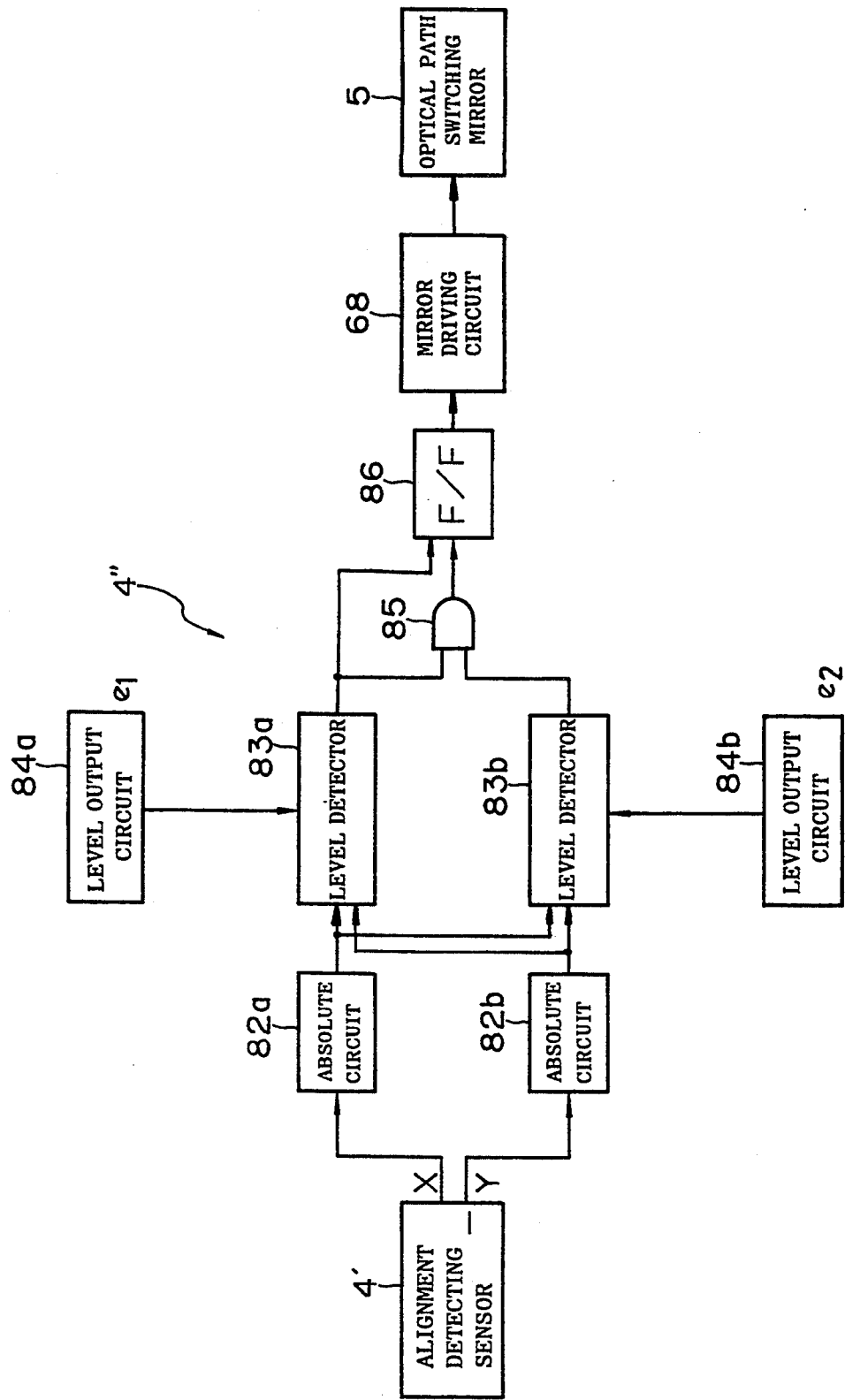

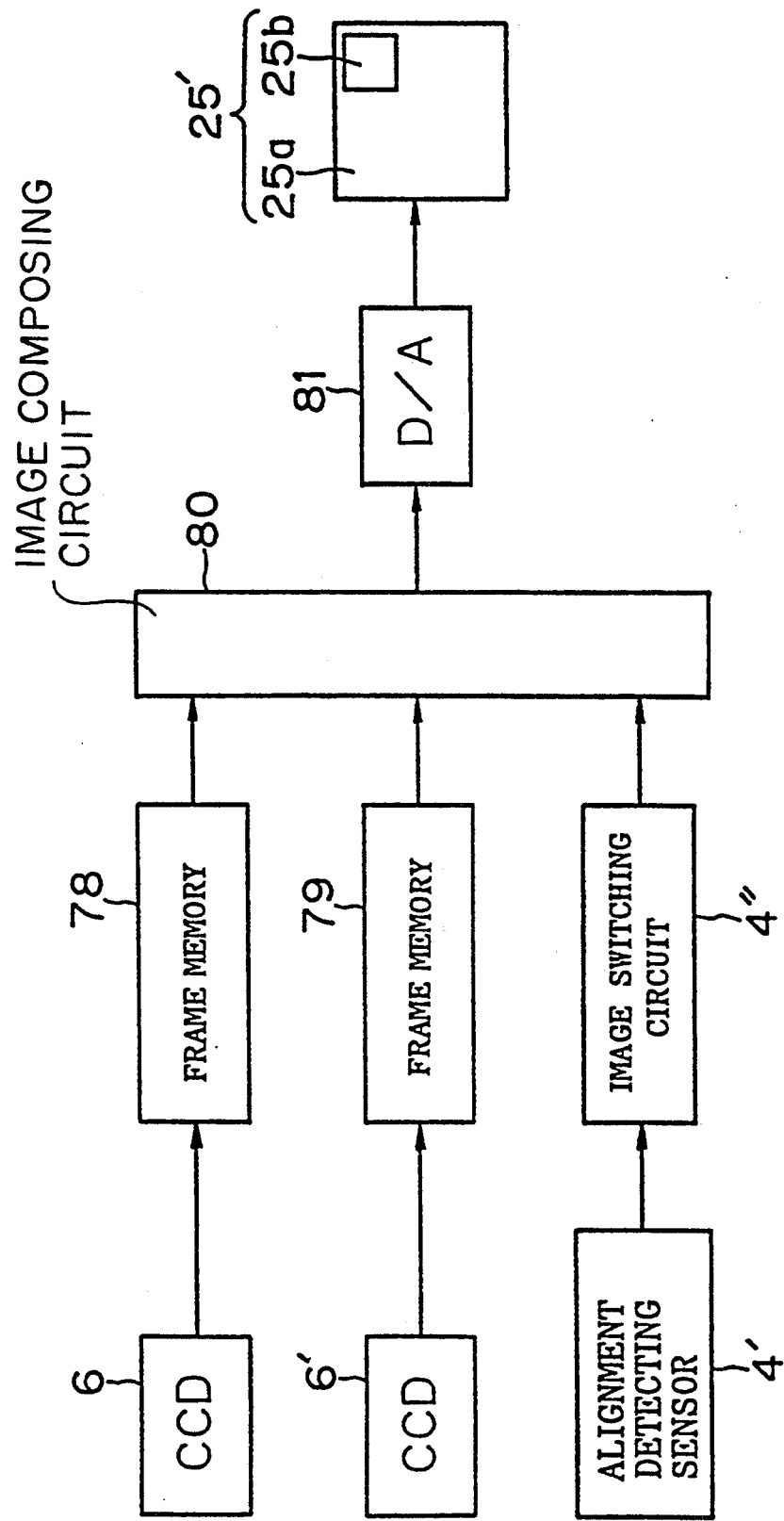

APPARATUS FOR PHOTOGRAPHING A CORNEAL ENDOTHELIUM

BACKGROUND OF THE INVENTION

1. Field of the Invention

This invention relates to an apparatus for photographing the endothelial layer of the cornea of a patient's eye by projecting illumination light onto the cornea.

2. Description of the Prior Art

Heretofore, there is known a contact type of apparatus for observing and photographing a corneal endothelium. In this type of apparatus, a liquid anesthetic is dropped into the eye before observing and photographing the endothelium therewith. The contact type of apparatus includes a cone lens which is in contact with the surface of the cornea. The apparatus, however, has drawbacks in that the cone lens injures the cornea because of contact of the lens with the corneal surface and much time is consumed for photography because of disinfection of the lens or the like. To remove those drawbacks, a non-contact type of apparatus has been developed in which a slit lamp is provided with an optical attachment for observing the endothelial layer.

The non-contact type of apparatus can generally determine its position relative to the eye in eye estimation. In the non-contact type of apparatus, illumination light emitted by a light source for observation is projected onto the cornea at an angle, reflected light from the cornea is guided to an eyepiece, and an operator observes the endothelial layer through the eyepiece and brings it into focus. A monitor screen can be also employed to take the focus.

By the way, the cornea itself is thin and its endothelium is composed of a single layer of thin flattened cells that lines the innermost portion of the cornea. Therefore, the endothelial layer must be highly magnified for observation. However, such a high magnification results in a big tremble of its image caused by involuntary movement of the eye (i.e., continuous slight motion of the eye when the eye is fixed). Therefore, the operator requires great skill to observe and photograph the corneal endothelial layer with the conventional non-contact type of apparatus. For example, the operator must act in a timely manner by pushing a photographing button as soon as the image is brought into focus. Further, since the non-contact type of apparatus is not predetermined to be precisely positioned relative to the eye, the operator must observe the dark field visible through the eyepiece until the image of the corneal endothelium appears or reflected light from the corneal surface is found out beside the image. This conventional apparatus largely depends on an operator's experience and strong intuitive judgement.

Further, since the alignment of the optical systems of the apparatus with the eye often requires much time, the patient is compelled for a long time to keep the eye open until photographing is completed, and hence undergoes much discomfort or pain.

SUMMARY OF THE INVENTION

A first object of the invention is to provide an apparatus for photographing a corneal endothelium, capable of determining the position of the optical system of the apparatus in relation to a patient's eye while observing the anterior segment of the eye.

A second object of the invention is to provide an apparatus for photographing a corneal endothelium, whereby difficulties imposed on an operator and a patient are lessened to the utmost.

To accomplish the objects, a corneal endothelium photographing apparatus according to first aspect of the invention is characterized by an observing optical system for observing the anterior segment of the patient's eye to align optical systems of the apparatus in the up, down, right, and left directions with respect to the eye and an illumination optical system for projecting each illumination light emitted by respective light sources for observation and photography onto the cornea of the eye. An observing and photographing optical system is provided for observing and photographing the corneal endothelium of the eye by receiving a reflected image thereof. The observing and photographing optical system includes an image receiving element for aligning the optical systems of the apparatus in the back and forth directions with respect to the eye. Display means for separately displaying respective images of the anterior segment and the corneal endothelium of the eye, and switching means for changing each display of the images of the anterior segment and the corneal endothelium to the other.

To accomplish the objects, a corneal endothelium photographing apparatus according to other objects of the invention is characterized by an observing optical system for observing the anterior segment of the patient's eye to align the optical systems of the apparatus in the up, down, right, and left directions with respect to the eye. An illumination optical system is provided for projecting each illumination light emitted by respective light sources for observation and photography onto the cornea of the eye. An observing and photographing optical system is provided for observing and photographing the corneal endothelium of the eye by receiving a reflected image thereof, wherein the observing and photographing optical system includes an image receiving element for aligning the optical systems of the apparatus in the back and forth directions with respect to the eye. A single display means is provided for simultaneously displaying respective images of the anterior segment and the corneal endothelium of the eye on two respective sections of the display means, and switching means change each display of the images of the anterior segment and the corneal endothelium to the other on the display means.

According to the corneal endothelium photographing apparatus according to the first aspects of the invention, alignment of the optical systems of the apparatus with respect to the eye is carried out in the up, down, right, and left directions while observing the anterior segment of the eye by means of the observing optical system. At the same time, an image of the anterior segment of the eye received by the two-dimensional image receiving element is displayed on the display means. When the image is brought into focus in the up, down, right, and left directions. Illumination light for observation is projected onto the cornea of the eye. The display image is then changed from the anterior segment to the corneal endothelium of the eye by means of the switching means. An operator aligns the optical systems of the apparatus in the back and forth directions with respect to the eye while observing the image of the corneal endothelium, and then photographs it. The following arrangement may be also adopted: Part of the reflected light from the cornea, which has been guided to the observing and photographing optical system, is guided to a line sensor, and the display switching means is actuated by detecting a given signal input into the line sensor when the anterior segment observing optical system is aligned in the up, down, right, and left directions with respect to the eye. Such an arrangement brings about good photography because, the switching means is actuated only with more accurate alignment.

According to the corneal endothelium photographing apparatus according the other aspects of the invention, illumination light is projected onto the cornea of the eye by means of the illumination optical system simultaneously with illumination of the anterior segment of the eye. An image of the anterior segment observed by the observing optical system is displayed large, for example. On the other hand, an image of the corneal endothelium observed and photographed by the observing and photographing optical system is displayed small, for example. An alignment of the optical systems in the up, down, right, and left directions with respect to the eye is carried out while seeing those small and large images. When the alignment is completed, the image of the anterior segment is displayed small whereas the image of the endothelium is displayed large. The optical systems of the apparatus are aligned in the back and forth directions with respect to the eye while observing the large image of the corneal endothelium, and then the endothelium is photographed.

BRIEF DESCRIPTION OF THE DRAWINGS

FIG. 18 is a block diagram showing a first variant of a display switching circuit according to the invention.

FIG. 27(b) shows the line sensor for FIG. 27(a).

FIG. 30 is a block diagram showing an image switching circuit according to the third embodiment.

DESCRIPTION OF THE PREFERRED EMBODIMENT

First Embodiment

Figure 1:
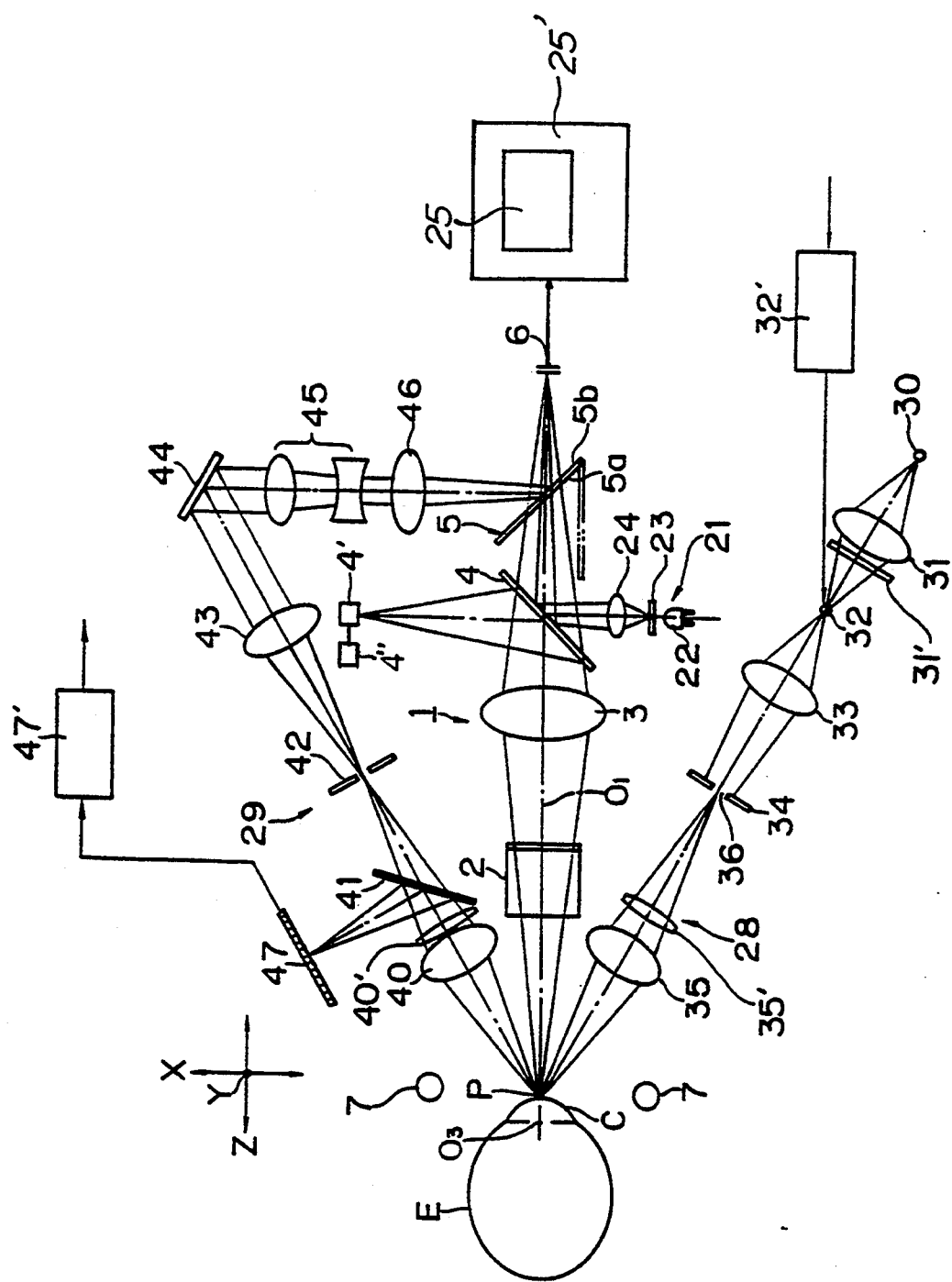
FIG. 1 shows an optical system of an embodiment of a corneal endothelium observing and photographing apparatus according to the invention.
Figures 2, 3A, 3B, 3C:
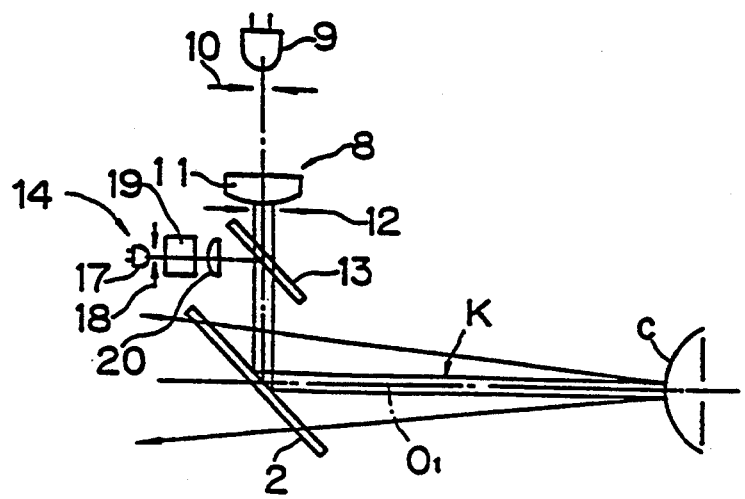
FIG. 2 shows an optical system for alignment according to the invention.
FIG. 3(a) shows an optical system for projecting an index on which a patient's eye is fixed according to the invention.
FIGS. 3(b) and 3(c) respectively show right and left eyes which may be fixed on the index projected by the system of FIG. 3(a).

FIG. 1 is a schematic plan view showing an optical system of an apparatus for observing and photographing the endothelial layer of the cornea of a patient's eye E. The numeral 1 denotes an optical system for observing the anterior segment of the eye E. The optical system 1 includes a half mirror 2, an objective lens 3, a half mirror 4, a mirror 5 for switching an optical path, and a CCD . The reference character $O_1$ denotes the optical axis of the optical system 1. The anterior segment of the eye E is illuminated by a light source 7. The half mirror 2 is part of an optical system 8 serving as means for projecting indices for alignment. As shown in FIG. 2, the optical system 8 includes a light source 9 for alignment, a pinhole plate 10, a projection lens 11, a diaphragm 12, and a half mirror 13. The pinhole plate 10 is disposed at the focus of the projection lens 11. After passing through the pinhole plate 10, index light is transformed into parallel rays of light by means of the projection lens 11. The parallel rays of light travel to the half mirror 2 via the half mirror 18. The parallel rays of light reflected by the half mirror 2 are guided to the cornea C of the eye E. The half mirror 18 is part of an optical system 14 for projecting indices on which the eye E is fixed.

As shown in FIG. 3 (a), the optical system 14 includes a projection optical system 15 for the left eye of the patient and a projection optical system 18 for the right eye of the patient. The projection optical systems 15 and 16 are separately arranged in the optical system 14 for the following reason. As for the right eye, the optical axis $O_2$ of the eye forms an angle of 5° rightward with respect to the visual line $S_1$ thereof (see FIG. 3 (b)) and as for the left eye, the optical axis $O_2$ of the eye forms an angle of 5° leftward with respect to the visual line $S_1$ thereof (see FIG. 3 (c)).

The projection optical systems 15 and 16 each include a light source 17, a pinhole plate 18, an optical member 19 for presenting a plural number of indices for eye's fixation, and a projection lens 20. The light source 17 for the right eye is automatically turned on when the right eye is examined, whereas the light source 17 for the left eye is automatically turned on when the left eye is examined. The on-off control of the light sources 17, 17 is performed by detecting the movement of an apparatus H, which will be hereinafter described, in the right or left direction, for example. Light emitted by the light source 17 is several times reflected on surfaces 19a and 19b of the optical member 19. The reflected light is then projected onto the eye E through the half mirrors 18 and 2. Thereby, a plural number of indices for eye's fixation are presented to the eye E. While the patient's eye is fixed on any index relative to the diopter, the alignment of the eye with the optical systems of the apparatus H is performed.

Figure 4:
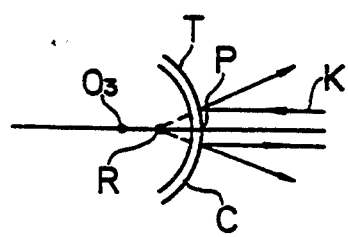
FIG. 4 shows reflection of index light for alignment according to the invention.

As shown in FIG. 4, rays of light K for alignment are reflected on the surface T of the cornea C as if they were emitted from the middle between the apex P of the cornea C and the center $O_3$ of curvature thereof. Therefore, the rays of light K for alignment forms a spot image R (virtual image) at the middle between P and $O_3$. The rays of light K reflected on the surface C are guided to the objective lens 3 through the half mirror 2. Part of the rays of light K is reflected by the half mirror 4 and the remainder passes through the same 4. The rays of light reflected by the half mirror 4 are guided to a light receiving element 4' for alignment. A PSD (position sensitive device), for example, is used as a light receving element. The function of the light receiving element 4' will be hereinafter described in detail.

Figure 5:
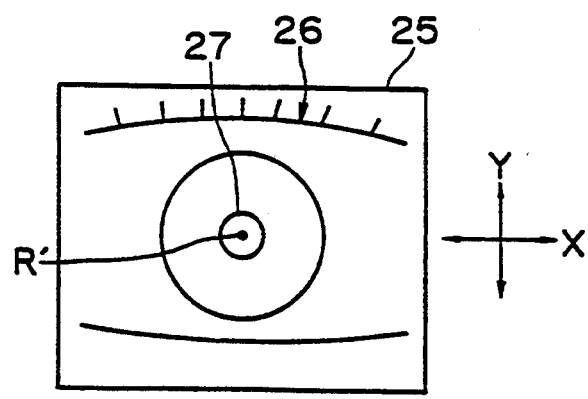
FIG. 5 shows an image of the anterior segment of the eye.
Figure 15:
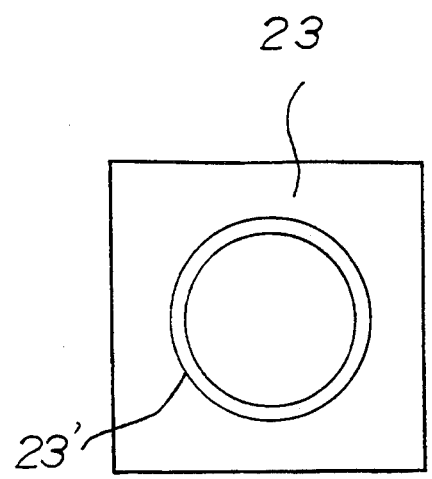
FIG. 15 is a plan view of a pattern plate of FIG. 1.

The mirror 5 for switching an optical path is usually disposed out of the optical path of the optical system 1 as shown by phantom lines in FIG. 1. The mirror 5 includes a light shading surface 5a on one side and a total reflection surface 5b on the other side. After passing through the half mirror 4, the rays of light are guided to the CCD 6 to form an image. The spot image R is formed on the CCD 6 according to the rays of light guided thereto. At the same time, an image of the anterior segment of the eye is formed on the CCD 8. The half mirror 4 reflects rays of light emitted from an optical system 21 for projecting an alignment pattern. The optical system 21 includes a light source 22, a pattern plate 23 for alignment, and a projection lens 24. As shown in FIG. 15, an annular pattern 23' is formed in the pattern plate 23. After passing through the annular pattern 23', the rays of light are reflected by the half mirror 4 and guided to the CCD 8. Thereby, an annular pattern image is formed on the CCD 8 which is connected with a monitor 25'. An image 28 of the anterior segment of the eye E and an annular pattern image 27 are displayed on a display 25 of the monitor 25' as shown in FIG. 5.

An operator carries out alignment while looking at the display 25.

First, the apparatus H, which will be hereinafter described, is moved in the up or down direction (in the Y direction) or in the right or left direction (in the X direction) so that the spot image R is located at the center of the annular pattern image 27. Thereby, the operator aligns the optical axis $O_z$ of the eye E with the optical axis $O_1$ of the apparatus H. The operator then moves the apparatus H toward or away from the eye E (in the Z direction) to determine an operating distance (that is, an axial distance between the apex of the cornea and the objective lens).

An optical system 28 for illumination and an optical system 29 for observation and photography are disposed on both sides of the optical system 1. The optical system 28 for illumination projects illumination light onto the cornea C of the eye E at an angle. The optical system 28 includes a light source 30 for illuminating the eye E when observed, a condenser lens 31, an infrared filter 31', a light source 32 for illuminating the eye E for photographed, a condenser lens 33, a slit plate 34, a projection lens 35, and an optical member 35' for compensating an optical path. The light source 30 is conjugate with the light source 32 with respect to the condenser lens 31.

The optical member 35' is disposed in the optical system 28 for the following reason.

Owing to different wavelengths, the focal point of illumination light for observing the corneal endothelium by means of infrared rays is different from that of illumination light for photographing it by means of visible rays. Therefore, in this embodiment, a convex lens as optical member 35' is inserted into the optical path of the optical system 28 for observation by means of infrared rays, whereas the convex lens is removed from the optical path thereof for photography by means of visible rays, in order to coincide the two focal points with each other. However, a parallel plate or concave lens as optical member 35' may be inserted into the optical path of the optical system 28 for photography by means of visible rays and be removed therefrom for observation by means of infrared rays.

Figure 6:
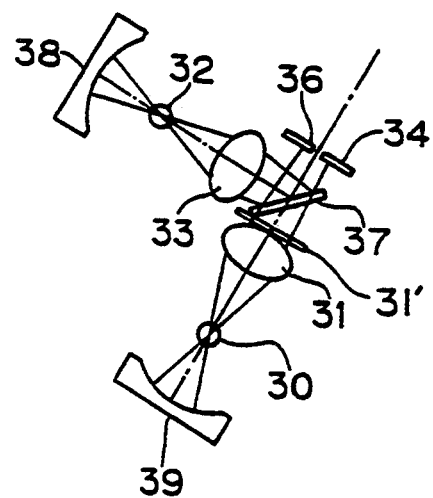
FIG. 6 shows a variant of a light source of an illumination optical system according to the invention.
Figure 16:
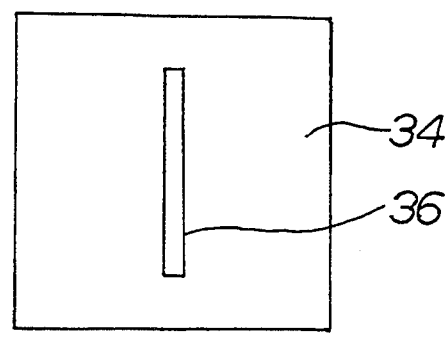
FIG. 16 is a plan view of a slit plate of FIG. 1.

For example, the light sources 30 and 32 are a halogen lamp and a xenon lamp, respectively. Rays of light emitted by the light source 30 are guided to the infrared filter 31' and transformed into infrared rays. The infrared rays are once condensed to the light source 32 and guided to the condenser lens 33 as if it were emitted by the light source 32. After passing through the condenser lens 33, the infrared rays are guided to the slit plate 34 which includes a long narrow rectangular slit 38 as shown in FIG. 16. After passing through the slit 36, they are guided to the projection lens 35. The slit plate 34 is approximately conjugate with the cornea C with respect to the projection lens 35 when aligned. Therefore, the slit infrared rays are projected onto the cornea C and they travel from the surface T of the cornea C to the inside thereof. A light source unit including the light source 30, the condenser lens 31, the infrared filter 31', the light source 32, and the condenser lens 33 may be arranged as shown in FIG. 6. Referring to FIG. 6, the numerals 37, 38, and 39 denote a dichroic mirror, a concave reflecting mirror, and a concave reflecting mirror, respectively. The dichroic mirror 37 for transmitting infrared rays and for reflecting visible rays is disposed between the condenser lens 31 and the slit plate 34.

Figure 17A:
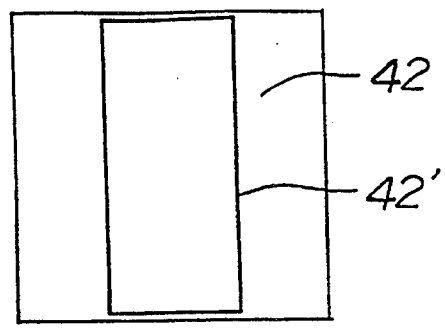
FIGS. 17(a) and 17(b) are plan views of respective embodiment of a diaphragm plate of FIG. 1.
Figure 17B:
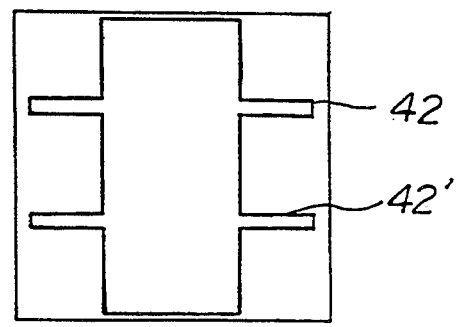

The optical system 29 for observation and photography includes an objective lens 40, a half mirror 41, a mask 42, a relay lens 43, a mirror 44, a variable power lens 46, a focusing lens 46, and a mirror 5. As shown in FIG. 17 (a) or 17 (b), the mask 42 includes a slit opening 42'. The mirror 5 is automatically inserted into the optical path of the optical system 1 according to the output from the sensor 4'. The mask 42 is approximately conjugate with the cornea C with respect to the objective lens 40 when aligned.

Figure 7:
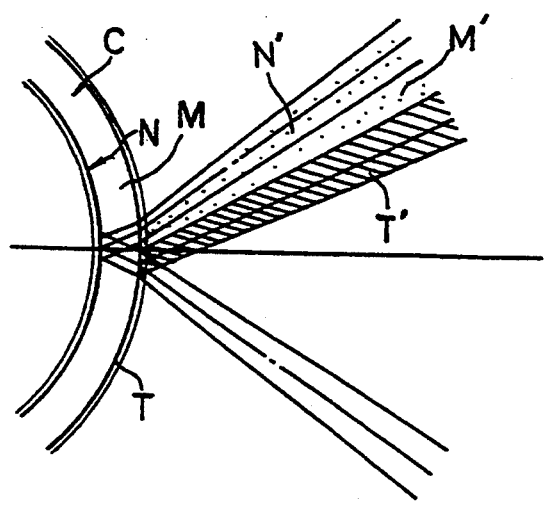
FIG. 7 shows reflection of slit light on the cornea.

The slit light rays are reflected by the cornea C. The reflection is schematically illustrated in FIG. 7. Part of the slit light rays is first reflected on the corneal surface T as a boundary between air and the cornea C. Of all the reflected light rays from the cornea C, reflected light rays T' from the surface T have the largest quantity of light. Reflected light rays N' from the endothelial layer N have a relatively small quantity of light. Reflected light rays M' from the stromal layer M have the smallest quantity of light. The reflected light rays N' are condensed by the objective lens 40 and guided to the half mirror 41. Part of the reflected light rays from the cornea C is reflected by the half mirror 41 and guided to a line sensor 47 for detecting an image of the endothelium layer in focus. The other part passing through the half mirror 41 is guided to the mask 42. An aerial image of the endothelium N is formed at the position of the mask 42 which serves to shade the remainder other than reflected light rays required to form the image of the endothelium N. The optical system 29 includes an optical member 40' for compensating an optical path length. The optical member 40' is disposed in the optical system 29 for a similar reason to the optical member 35' in the optical system 28. In this embodiment, the optical member 40' is a convex lens which is inserted into the optical path of the optical system 29 when observed by means of infrared rays and is removed therefrom when photographed by means of visible rays. However, a parallel plate or concave lens as optical member 40' may be inserted into the optical path of the optical system 29 when photographed by means of visible rays and be removed therefrom when observed by means of infrared rays.

Figure 8:
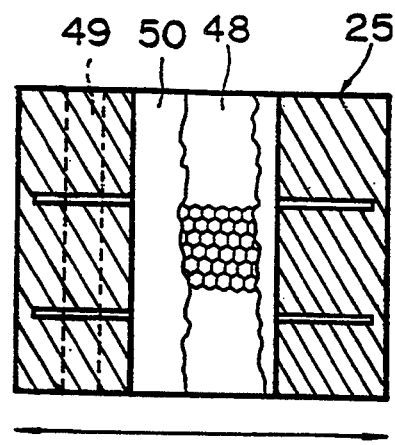
FIG. 8 shows an image of the corneal endothelium of the eye.

The reflected light rays for forming the image of the endothelial layer N are guided to the mirror 5 through the relay lens 43, the mirror 44, the variable power lens 45, and the focusing lens 46. They are then reflected by the mirror 5 and focused on the CCD 8. Thereby, the image of the endothelial layer N is displayed on the display 25 as shown in FIG. 8. Referring to FIG. 8, the numeral 49 indicated in stitch lines denotes a bright image formed by the light rays reflected by the corneal surface T and the numeral 50 denotes an image formed by the light rays M' reflected by the stromal layer M, on the assumption that the mask 42 transmits all the reflected light rays.

Figure 9:
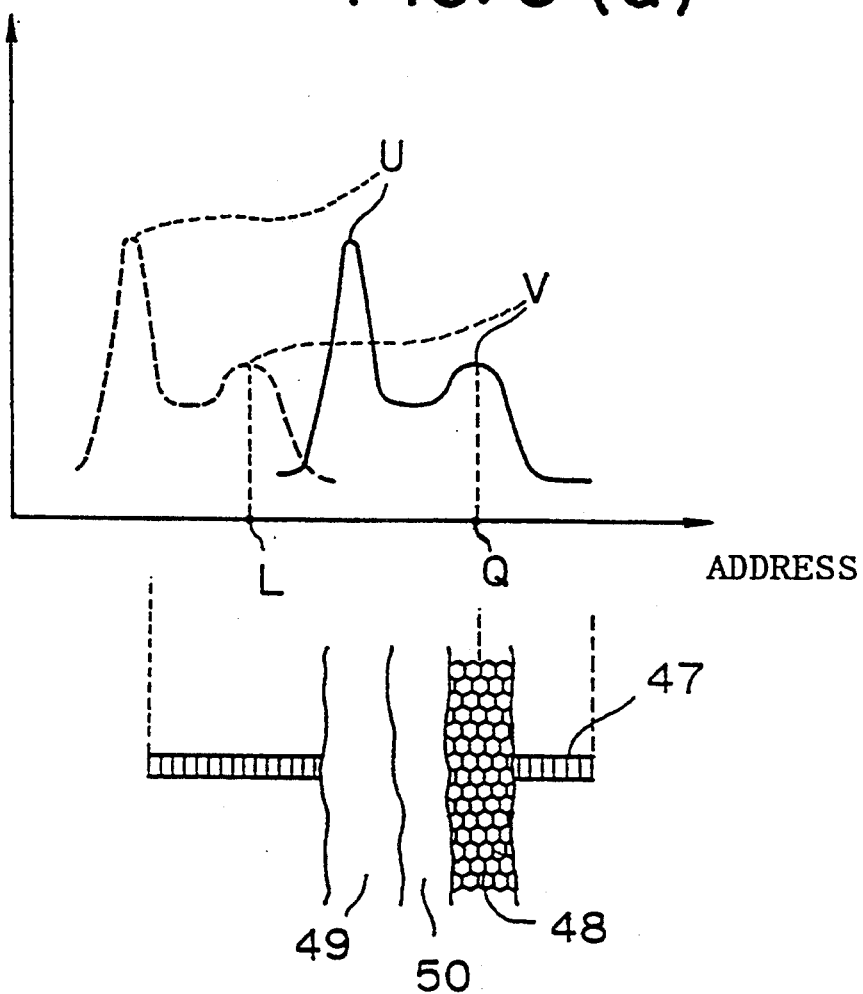
FIGS. 9(a) and 9(b) show the relation between the image of the corneal endothelium and the quantity of light received by a line sensor.

Toward the respective layers of the cornea, the line sensor 47 is arranged as shown at the bottom of. Therefore, with respect to the line sensor 47, the intensity of the reflected light rays is distributed as shown at the top of FIG. 9. Referring to top of FIG. 9, the reference character U denotes the peak intensity of the light rays reflected by the corneal surface T and the reference character V denotes the peak intensity of the light rays reflected by the endothelial layer N. The peaks U and V correspond to the images 49 and 48, respectively.

As shown in FIG. 1, the output from an element in each address of the line sensor 47 is input to a focusing judging circuit 47' for judging an image of the endothelium in focus or out of focus. The focusing judging circuit 47' memorizes signals corresponding to the intensity shown in FIG. 9. The focusing judging circuit 47' decides the address of the peak V by means of an arithmetic processor as a well-known means. To judge whether the apparatus H and the eye e are properly located to gain exact focusing, the focusing judging circuit 47' detects the coincidence of the address L of the peak V with a given address (the central address Q, for example) of the line sensor 47. That is, the address L of the peak V is changed by moving the apparatus H toward or away from the anterior segment of the eye E (that is, by moving the optical system of the apparatus in the Z direction in FIG. 1). The apparatus H is arranged so that the corneal endothelium N is in focus when the address L of the peak V coincides with the central address Q. Supposing that the peak v is positioned at the address L of the line sensor 47 as shown in a stitch line in FIG. 9, the address L approaches the central address Q by moving the apparatus H toward the eye E. When the address L of the peak V coincides with the central address Q, the focusing judging circuit 47' outputs a photographing signal toward a control circuit 32' for turning on the light source 32. Thereby, light rays are emitted by the light source 32, the eye is illuminated, and an image of the endothelium is automatically taken. Preferably, the light source 30 is turned off when photographed.

Figure 10:
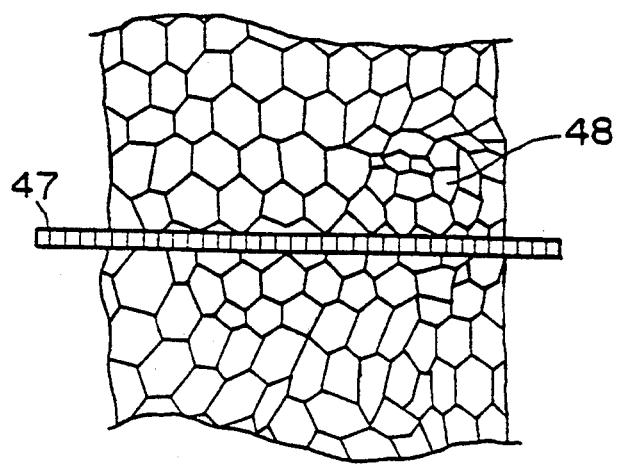
FIG. 10 illustrates another method of detecting the image of the corneal endothelium in focus.
Figure 11:
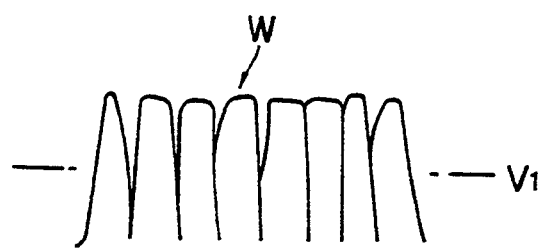
FIG. 11 shows the output of the line sensor of FIG. 10.

A judgement whether the image 48 of the endothelium N is in focus or out of focus may be formed in the following way. As shown in FIG. 10, the image 48 if formed at the line sensor 47. When the image 48 is out of focus. The output from each element of the line sensor 47 is low. When in focus, the image 48 at the line sensor 47 is good contrast, and hence the intensity of the reflected light rays from the cornea C is distributed with respect to the line sensor 47 as shown in FIG. 11. Therefore, a judgment as to the image 48 in focus or out of focus is formed by detecting a level W of the signal from each element of the line sensor 47 more than a given level $V_1$.

Figure 12:
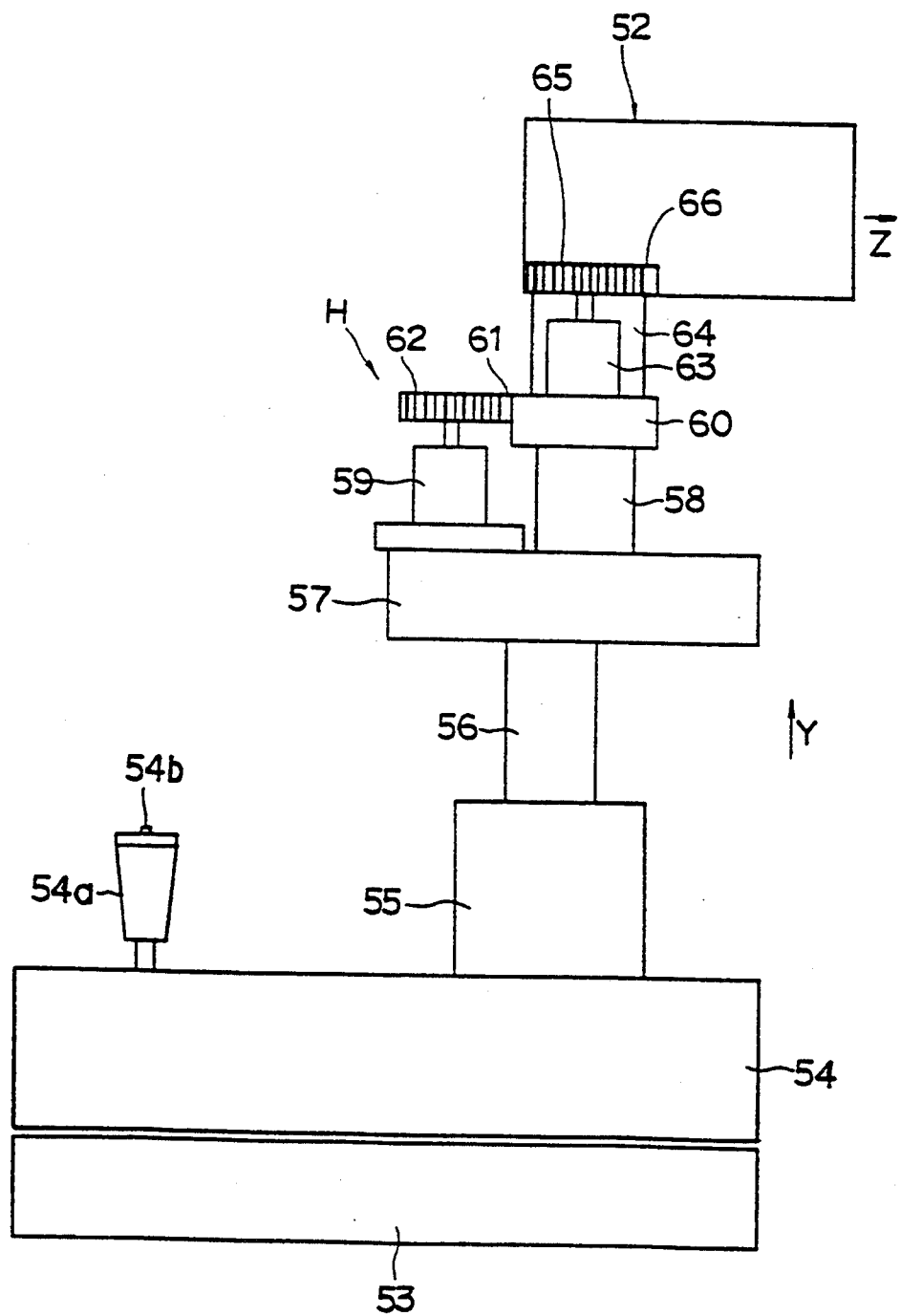
FIG. 12 is a side view showing the whole construction of the apparatus according to the invention.
Figure 13:
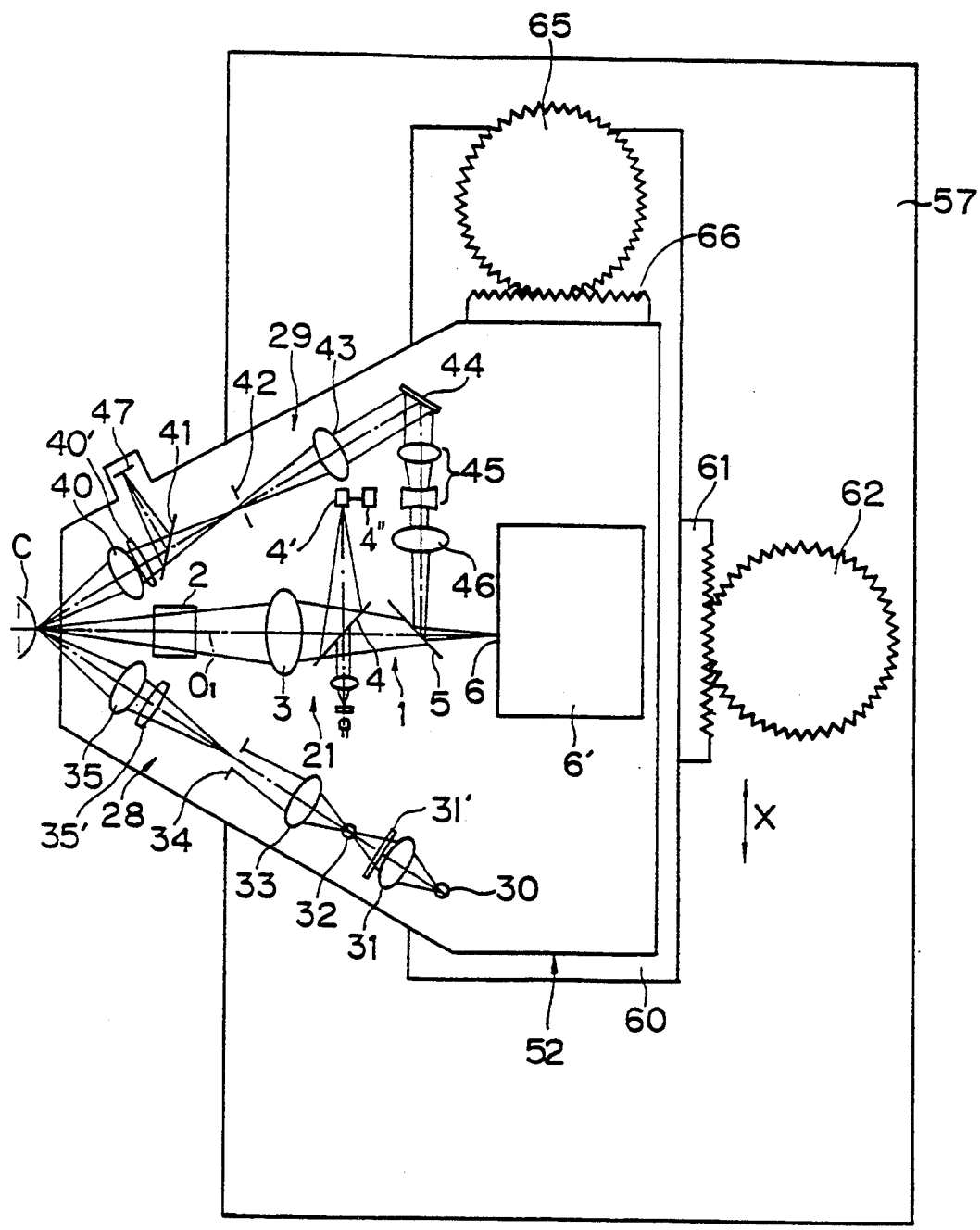
FIG. 13 is a partial top view of the apparatus according to the invention.

As shown in FIG. 12, the optical systems 1, 28, and 29 are contained in a case 52 of the apparatus H. An electric source, not shown, is contained in a base 53. A frame 54 is mounted on the base 58 so as to move in all directions. The numerals 54a and 54b denote a control lever for the frame 54 and a photographing switch for a manual photographing mode, respectively. A motor 55 and a supporting pillar 58 are mounted on the frame 54. The motor 55 is connected with the supporting pillar 56 by a pinion and a rack, not shown. The supporting pillar 56 is moved up and down by the motor 55. A pillar 58 and a motor 59 are mounted on a table 57. Another table 60 is movably mounted on the pillar 58. As shown in FIG. 13, a rack 61 is disposed behind the table 60. A pinion 62 is connected with an output shaft of the motor 59. The pinion 62 is engaged with the rack 61. A motor 63 and a pillar 64 are mounted on the table 60. A pinion 65 is connected with an output shaft of the motor 63. The case 52 is movably mounted on the pillar 64. A rack 66 engaged with the pinion 65 is disposed at the side of the case 52. In FIG. 13, the numeral 6' denotes a signal processing unit.

The motors 55, 59, and 63 serve to automatically align the apparatus H in the Y, X, and Z directions, respectively, with the eye E. These motors 55, 59, and 63 can work in an automatic aligning mode. In other words, the motors 55, 59, and 63 each serve as a means for driving the aparatus H according to the output from a light receiving means.

Figure 14:
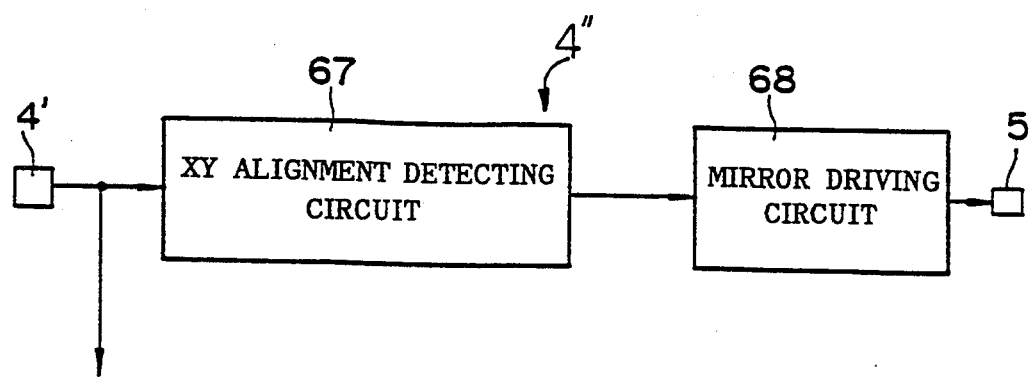
FIG. 14 is a block diagram showing an example of a circuit for switching an image displayed on a display means.

In the automatic aligning mode, the operator handles the control lever 54a while looking at the image 26 of the anterior segment of the eye E and the spot image R' displayed on the display 25 in order to move the frame 54 and bring the spot image R' close to a given circle 27. Thereby, the reflected light rays for forming the spot image R' are guided to the sensor 4'. The sensor 4' detects positions of the spot image R' in the X and Y directions. The positions detected thereby are input into a detection circuit 67, shown in FIG. 14, for alignment in the X and Y directions.

The X-Y alignment detecting circuit 67 judges whether alignment in the X and Y directions is completed. For example, when the optical path switching mirror 5 is out of the optical path of the optical system 1 and each alignment in the X and Y directions is completed, an alignment signal H (high-level alignment signal) is output to a mirror driving circuit 68 which forms part of an image switching circuit 4". When not completed, an alignment signal L (low-level alignment signal) is output to the mirror driving circuit 68. By the input of the alignment signal H, the mirror driving circuit 68 is driven to insert the mirror 5 into the optical path of the optical system 1. On the other hand, by the input of the alignment signal L, the circuit 68 is not driven and the mirror 5 remains out of the optical path of the optical system 1. When the alignment signal H is changed to the alignment signal L with the mirror 5 kept inserted in the optical path of the optical system 1, the mirror driving circuit 88 stops working and the mirror 5 is removed from the same path by means of, for example, a spring (not shown).

Position signals of the X and Y directions detected by the sensor 4' are input into a signal processing circuit 6'. The signal processing circuit 6' drives the motor 59 according to the position signal of the X direction so that the optical axis $O_1$ of the optical system 1 approaches the optical axis $O_2$ of the eye E in the X direction. Also, the signal processing circuit 6' drives the motor 55 according to the position signal of the Y direction so that the optical axis $O_1$ of the optical system 1 approaches the optical axis $O_2$ of the eye E in the Y direction. The table 60 is moved in the X direction by the motor 59, whereas the table 57 is moved in the Y direction by the motor 55. In such a way, the optical axes $O_1$ and $O_2$ are automatically adjusted to each other. On the other hand, the motor 83 moves the case 52 in the Z direction according to a difference between the respective addresses Q and L detected by the one-dimensional line sensor 47 so that the address L of the peak coincides with the central address Q. Thereby, the alignment of the optical systems of the apparatus H with the eye E is automatically completed and then the corneal endothelium N is automatically photographed.

The image switching circuit 4" is not restricted to the same disclosed in the embodiment mentioned above, hence the following variant forms are possible.

Variant 1

Figure 19:
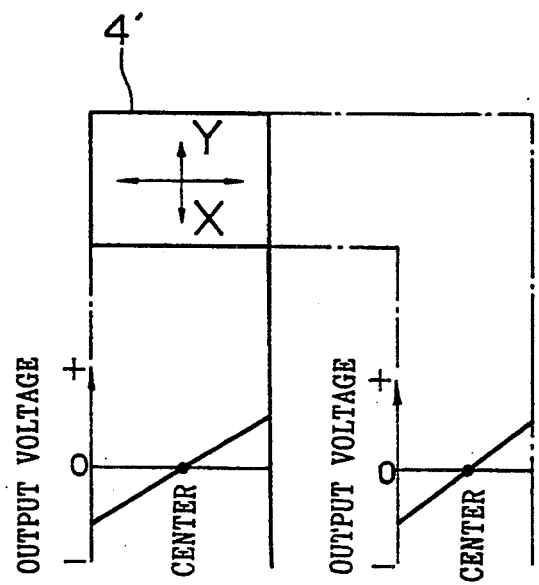
FIG. 19 illustrates an alignment detecting sensor.

As shown in FIG. 18, an image switching circuit 4" according to this variant includes a pair of absolute circuits 82a, 82b as maintaining means, level detectors 83a, 83b, level output circuits 84a, 84b, an AND circuit 85, a flip-flop circuit 86, and a mirror driving circuit 68. The absolute circuits 82a, 82b, as shown in FIG. 19, serve to transform a plus or minus voltage (each in the X and Y directions) output from the alignment detecting sensor 4' into an absolute voltage.

Figure 20:
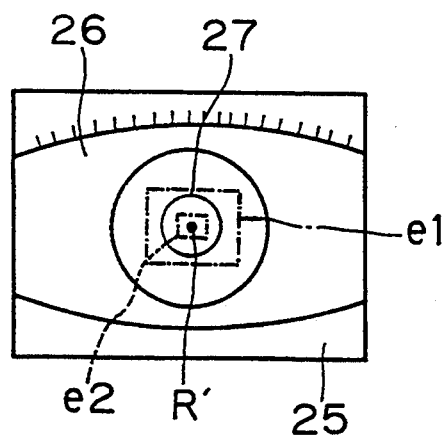
FIG. 20 is a front view of a monitor showing a display at the time when X-Y alignment is carried out with the alignment detecting sensor.

The level output circuits 84a, 84b output a base level signal to the level detectors 83a, 83b, respectively. The base level signal output from the level output circuit 84a corresponds to a square alignment area e1 formed larger than an annular pattern image 27, as shown in FIG. 20. On the other hand, the base level signal from the level output circuit 84b corresponds to a square alignment area e2 formed smaller than the annular pattern image 27. Since the annular pattern image 27 shown in FIG. 20 is presented only for comparison, it is not necessarily required in this variant.

The flip-flop circuit 86 is arranged so as to tranform L-level (low-level) into H-level (high-level) when the detector 83a and the AND circuit 85 each output H-level, and to maintain H-level while the detector 83a remains outputting H-level even if the AND circuit 85 transforms the output from H-level into L-level while the flip-flop circuit 86 remains H-level.

When the spot image R' is located out of the area e1, the AND circuit 85 outputs L-level, the mirror driving circuit 68 does not work, and the mirror 5 is out of the optical path of the optical system 1 because the level detectors 83a, 83b both output L-level.

When the spot image R' is located within the area e1, and out of the area e2 as well, the AND circuit 85 outputs L-level, the mirror driving circuit 68 does not work, and the mirror 5 is out of the optical path of the optical system 1 because the level detector 83b outputs L-level while the level detector 83a outputs H-level.

When the spot image R' is located within the area e2 by aligning the optical systems with the eye, the AND circuit 85 outputs H-level and hence the output of the flip-flop circuit 88 is transformed from L-level to H-level, the mirror driving circuit 68 starts working, and the mirror 5 is inserted into the optical path of the optical system 1.

In spite of a small misalignment caused by eye movement, when the spot image R' is located within the area e1, the level detector 83a outputs H-level, the flip-flop circuit 86 keeps H-level, and accordingly the mirror driving circuit 68 goes on working and the mirror 5 remains inserted in the optical path of the optical system 1. According to Variant 1, therefore, a disadvantage of repeated switching of a displayed image caused by eye movement can be avoided.

Variant 2

Figure 21:
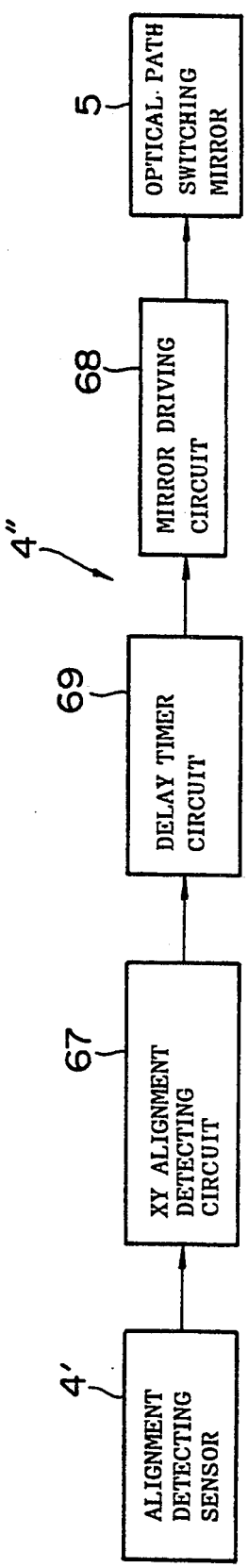
FIG. 21 is a block diagram showing a second variant of the display switching circuit.

As shown in FIG. 21, an image switching circuit 4" according to this variant includes the X-Y alignment detecting circuit 67, a mirror driving circuit 68, and a delay timer which serves to delay X and Y alignment signals for a given time. This arrangement permits the mirror driving circuit 68 to respond after some delay with respect to the change of the input of the X-Y alignment signals. Therefore, the mirror 5 keeps the state before the change of the signals, and such a disadvantage as in Variant 1 is avoidable according to this variant.

Variant 3

Figure 22:
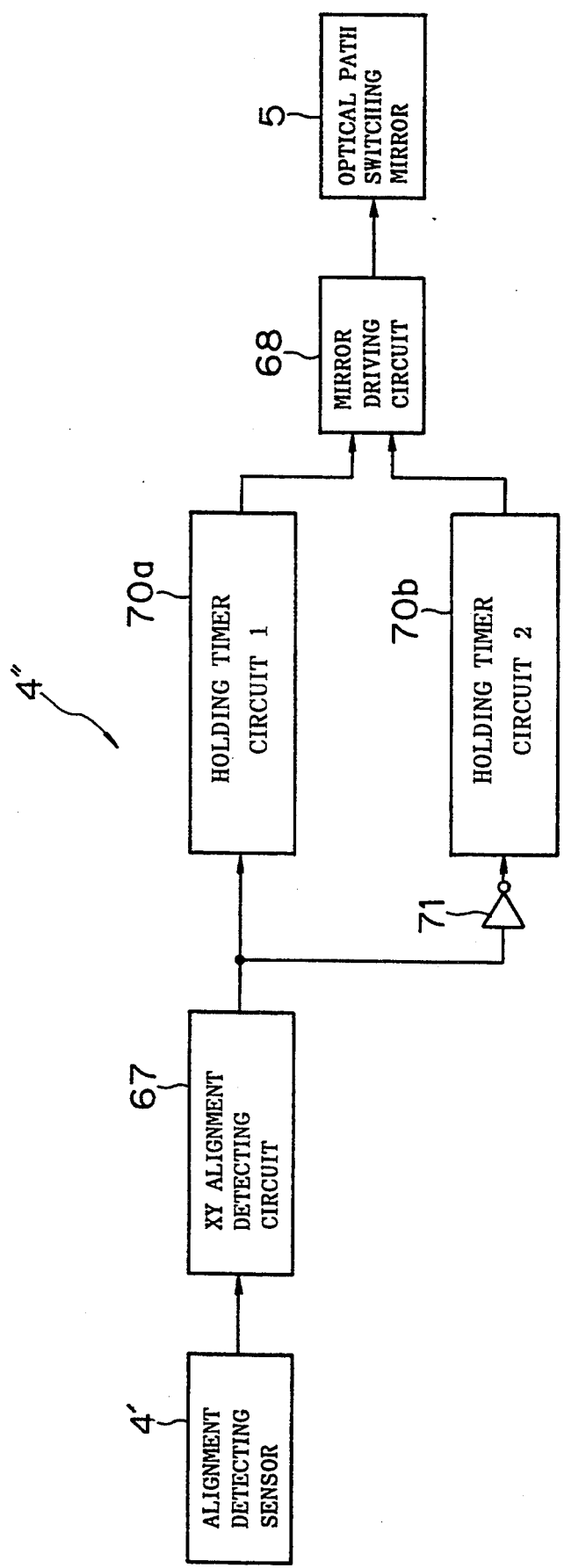
FIG. 22 is a block diagram showing a third variant of the display switching circuit.

As shown in FIG. 22, an image switching circuit 4" according to this variant includes the X-Y alignment detecting circuit 67, a mirror driving circuit 68, a pair of timer circuits 70a, 70b as maintaining means, and a reversing device 71 for reversing the output of the timer circuit 70b. In this variant, the mirror 5 is electrically driven to insert into or remove from the optical path without an elastic means such as a spring.

When the X-Y alignment detecting circuit 67 outputs an alignment signal H, the timer circuit 70a outputs H-level after a given delay, the mirror driving circuit 68 is driven after a given delay, and the mirror 5 is inserted into the optical path of the optical system 1. On the other hand, when the X-Y alignment detecting circuit 67 outputs an alignment signal L, the timer circuit 70b outputs H-level after a given delay, the mirror driving circuit 68 is driven after a given delay, and the mirror 5 is removed from the optical path of the optical system 1.

By shortening the given delay for the timer circuit 70a and lengthening the given delay for the timer circuit 70b, the mirror is inserted into the optical path without relatively delaying.

Variant 4

Figure 23:
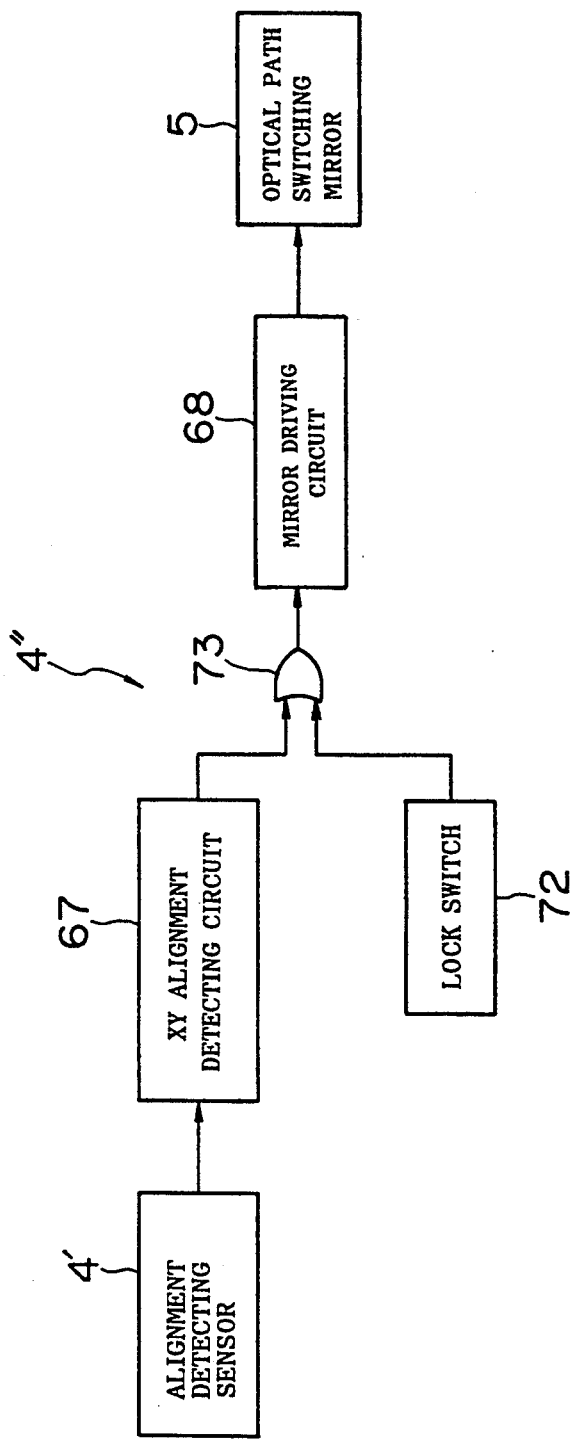
FIG. 23 is a block diagram showing a fourth variant of the display switching circuit.

As shown in FIG. 23, an image switching circuit 4″ according to in this variant includes the X-Y alignment detecting circuit 67, the mirror driving circuit 68, a lock switch 72 as holding or maintaining means, and an OR circuit 73. The lock switch 72 serves to actuate the mirror driving circuit 68 by hand control. When the lock switch 72 is turned on with the mirror 5 kept inserted in the optical path of the optical system 1, the driving circuit 68 is locked to keep the mirror 5 inserted in the optical path. Therefore, unless the lock switch 72 is turned off, the mirror 5 remains in the optical path regardless of the state of the output of the X-Y alignment detecting circuit 67.

Variant 5

Figure 24:
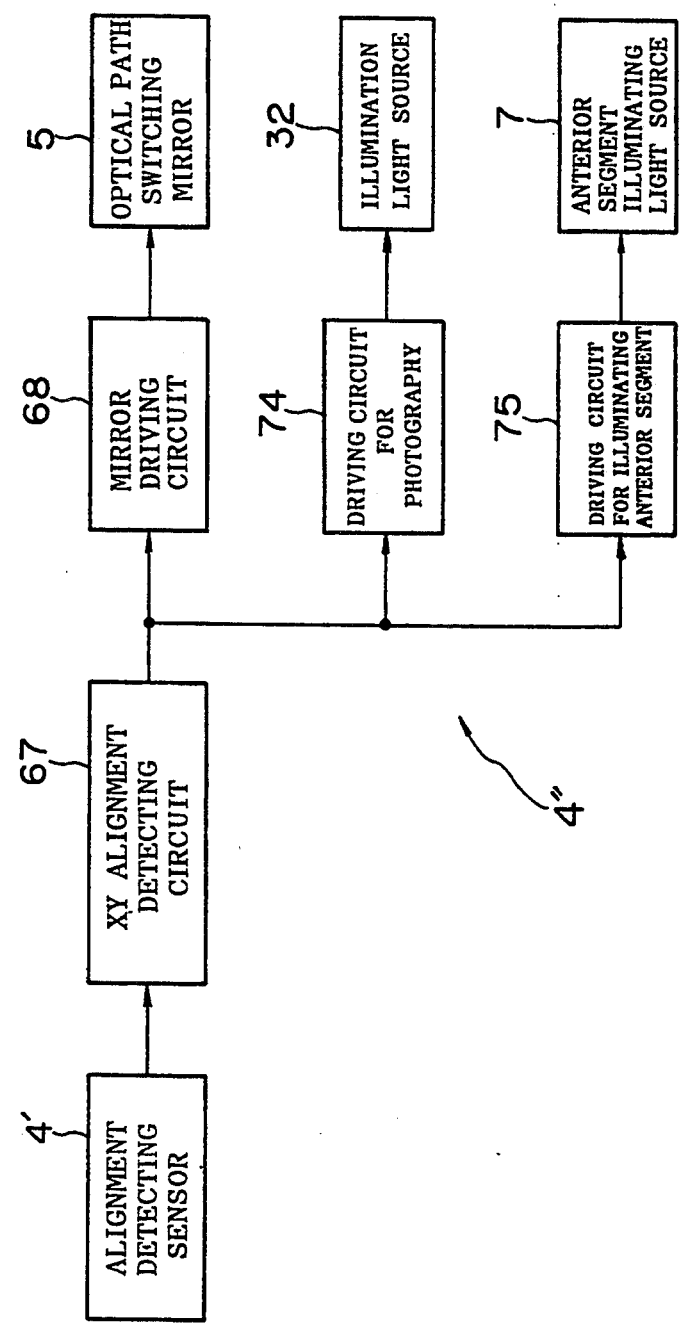
FIG. 24 is a block diagram showing a fifth variant of the display switching circuit.

As shown in FIG. 24, an image switching circuit 4″ according to this variant includes the X-Y alignment detecting circuit 67, the mirror driving circuit 68, an illumination driving circuit 74 for photography, and a driving circuit 75 for illuminating the anterior segment. The circuits 74 and 75 are turned on or off synchronizing with the drive of the mirror 5. That is, the driving circuit 74 for photography is turned on simultaneously with the transformation of an X-Y alignment signal into H-level, whereas the driving circuit 75 for illuminating the anterior segment is turned off simultaneously with the transformation of an X-Y alignment signal into H-level.

Variant 6

Figure 25:
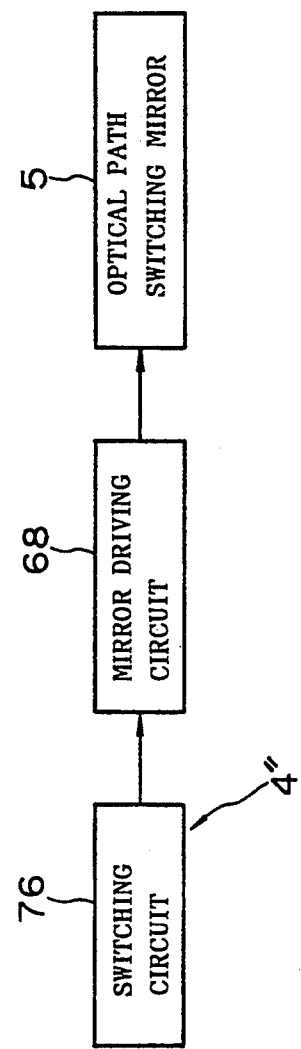
FIG. 25 is a block diagram showing a sixth variant of the display switching circuit.

As shown in FIG. 25, an image switching circuit 4″ according to this variant includes a switch circuit 76, and the mirror driving circuit 68. The switch circuit 78 is electrically connected with an image switching switch (not shown) worked by hand. The image switching circuit 4″ according to this variant is arranged so that the alignment is carried out while seeing the anterior segment, and the mirror 5 is driven by the hand-worked switch when each alignment in the X and Y directions is completed.

Variant 7

Figure 26:
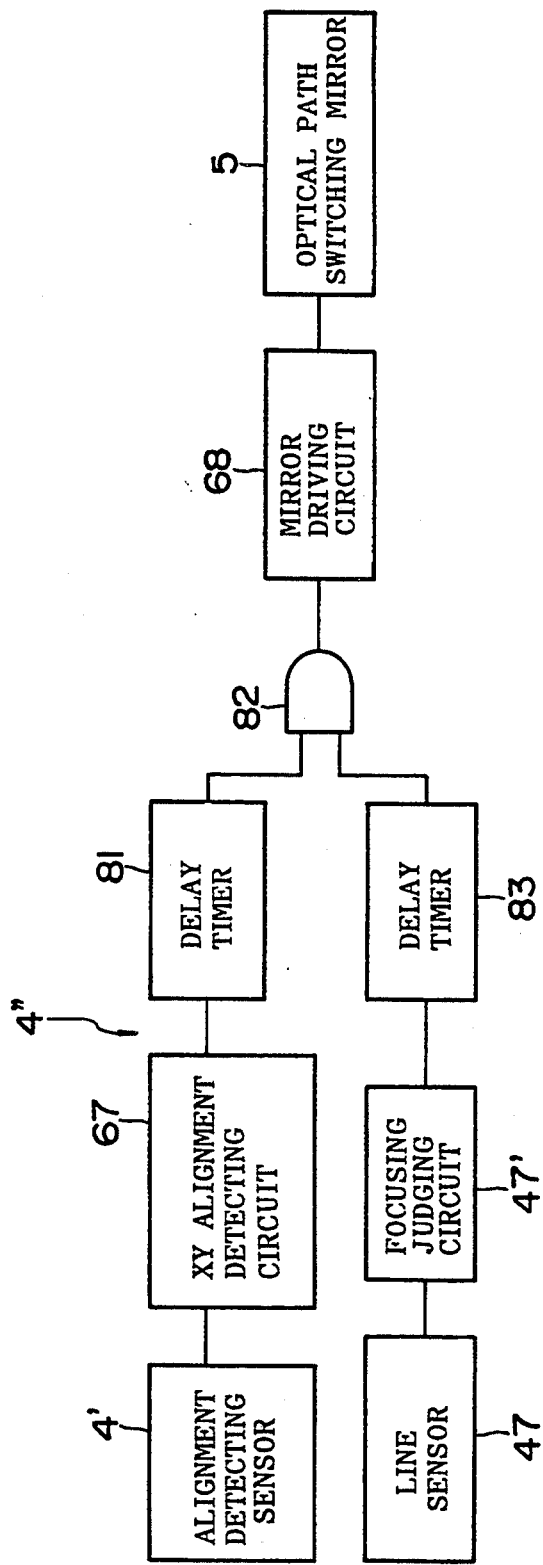
FIG. 26 is a block diagram showing a seventh variant of the display switching circuit.
Figure 27A:
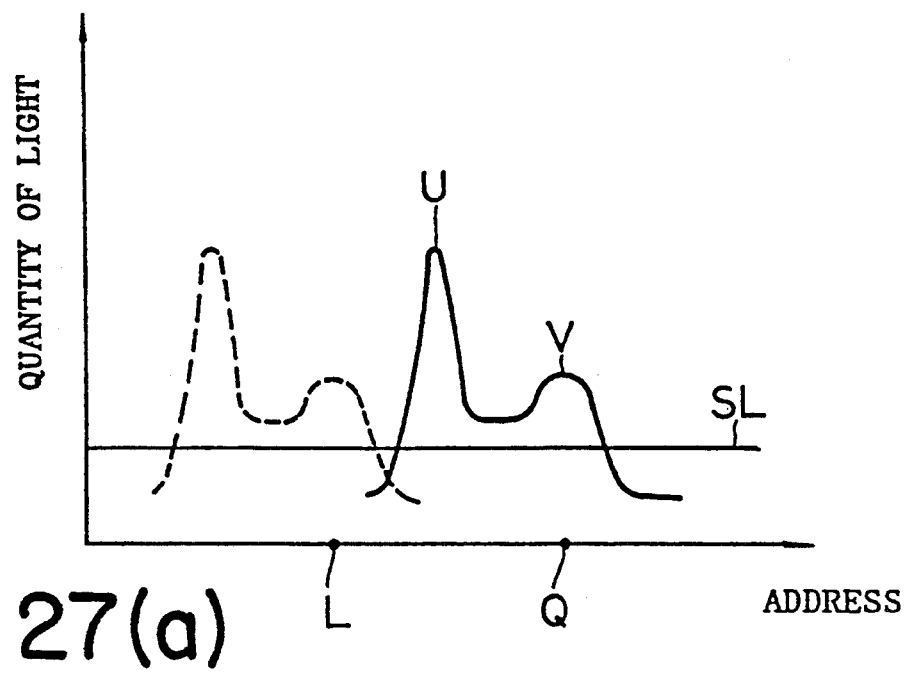
FIGS. 27(a) and 27(b) show the relation between an image of the corneal endothelium according to the seventh variant and the quantity of light received by the line sensor.
Figure 27B:
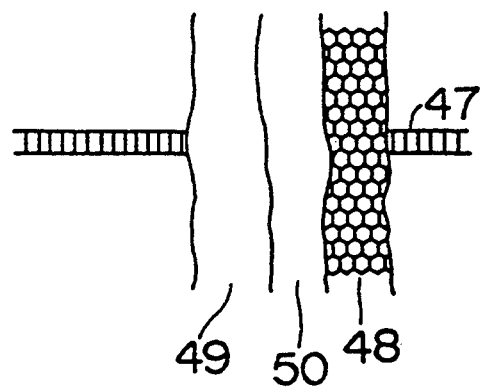

As shown in FIG. 26, an image switching circuit 4″ according to this variant includes the X-Y alignment detecting circuit 67, a delay timer 81, the AND circuit 82, the line sensor 47, the focusing judging circuit 47′, and a delay timer 83. An alignment signal output from the X-Y alignment detecting circuit 67 is input to the AND circuit 82 via the delay timer 81. On the other hand, an output signal of the element at each address of the line sensor 47 is input to the focusing judging circuit 47′. If the light source 30 always emits illumination light, when the signal output from any element of the line sensor 47 (see bottom of FIG. 27) surpasses a given slice level SL as shown in the top of FIG. 27, the focusing judging circuit 47′ outputs a switching signal to the delay timer. The AND circuit becomes H-level when the alignment signal H and a switching signal are input to the AND circuit, and then the mirror driving circuit 68 is driven. According to this variant, a displayed image is switched when each alignment in the X, Y, and Z directions is preferable.

Second Embodiment

Figure 28:
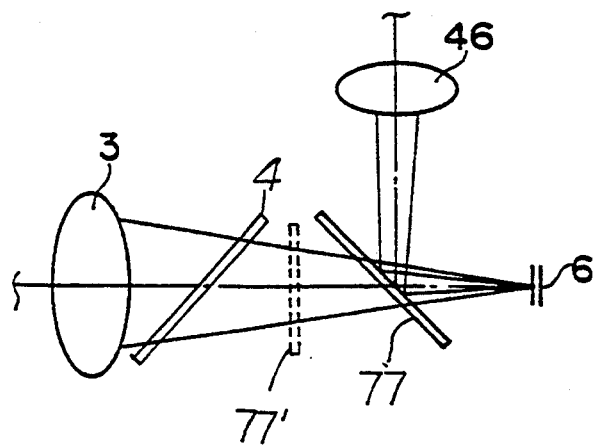
FIG. 28 shows a second embodiment of a corneal endothelium photographing apparatus according to the invention, wherein an optical path switching mirror shown in FIG. 1 is replaced with a dichroic mirror.

FIG. 28 shows a second embodiment of a corneal endothelium photographing apparatus according to the invention. In this embodiment, a dichroic mirror 77 is used instead of the mirror 5. The light source 7 for illuminating the anterior segment of the eye for observation is of infrared rays. Index light rays for alignment and light rays for forming a pattern image are also infrared rays. The dichroic mirror 77 serves to transmit index light rays for alignment reflected by the cornea C and light rays reflected by the anterior segment of the eye E and to reflect slit light rays reflected by the cornea C. Such an arrangement permits a display image to be switched from an image 26 of the anterior segment to an image 48 of the corneal endothelium without moving the dichroic mirror 77. In other words, images of the anterior segment, of the spot, and of the pattern can disappear from the display 25 by turning off the light sources 7, 9, and 22. To vanish the images therefrom without turning off the light sources, between the half mirror 4 and the dichroic mirror 77 may be disposed a liquid crystal shutter 77′ for shading light rays simultaneously with the completion of each alignment in the X and Y directions.

Third Embodiment

Figure 29:
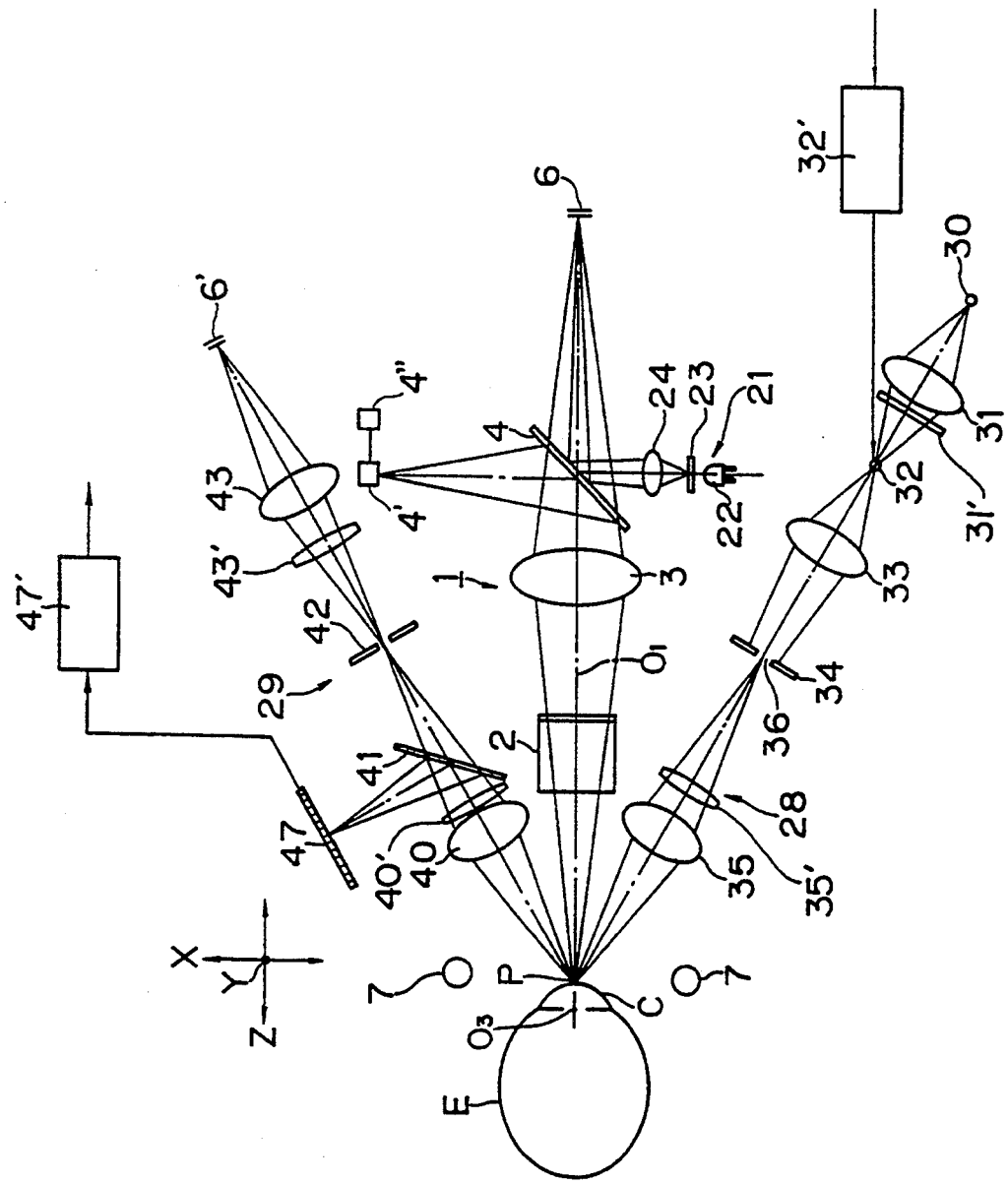
FIG. 29 shows a third embodiment of a corneal endothelium photographing apparatus according to the invention.

FIGS. 29 to 31 show a third embodiment of a corneal endothelium photographing apparatus according to the invention. In these FIGS. 29 to 31, the same numerals are given to the same components as in the first embodiment, and a description of the same will be omitted.

Figure 31A:
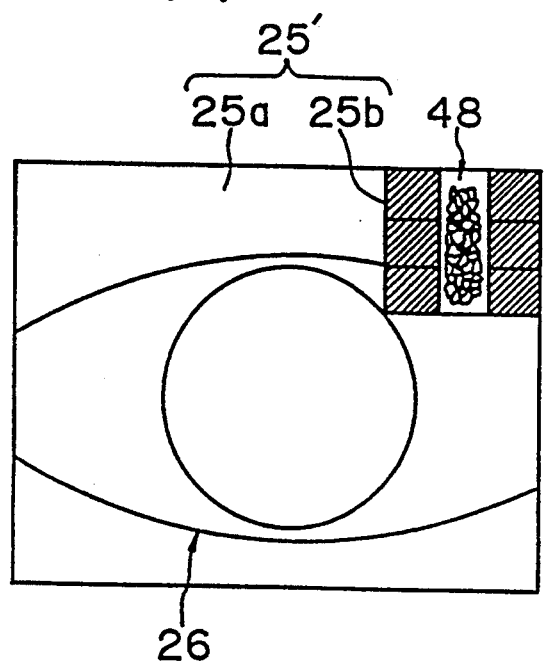
FIGS. 31(a) and 31(b) show a display at the time when X-Y alignment is carried out, a display at the time when the corneal endothelium is observed, respectively.
Figure 31B:
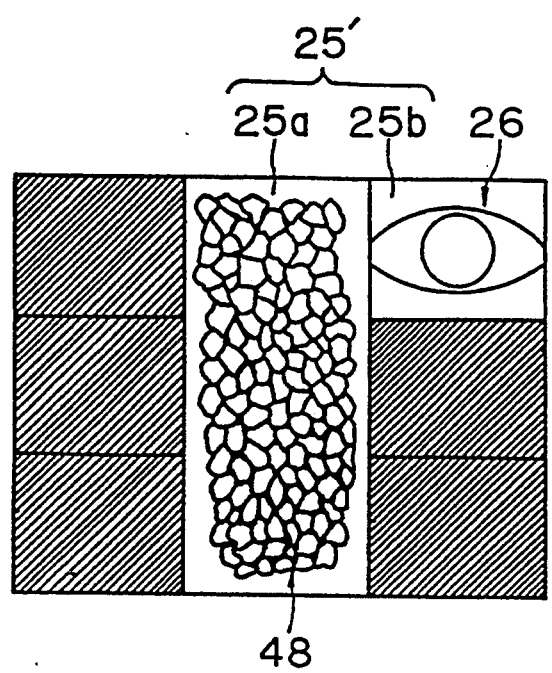

Referring now to FIG. 29, the optical system 1 includes the half mirror 2, the objective lens 3, the half mirror 4, and the first CCD. The observing and photographing optical system 29 includes the objective lens 40, the half mirror 41, the mask 42, the relay lens 43, and the second CCD 6′. Part of the reflected light guided to the objective lens 3 is reflected by the half mirror 4. The remainder is received by the CCD through the half mirror 4. The light reflected by the half mirror 4 is guided to the alignment detecting sensor 4′. An X-Y alignment signal is output from the alignment detecting sensor 4′ to the image switching circuit 4″. The reflected light from the corneal endothelium is condensed to the relay lens 43 and then its image is formed on the second CCD 6′. As shown in FIG. 30, the images of the anterior segment and the endothelium received on the first and second CCDs 6 and 6′ respectively are output to an image composing circuit 80 via frame memories 78 and 79. The respective images composed by the circuit 80 are displayed on the display 25 of the monitor 25′ via a D/A converter 81. The display 25 consists of large and small displays 25a and 25b. As shown in FIG. 31(a), before completing the X-Y alignment, the large display 25a displays an image 26 of the anterior segment, whereas the small display 25b displays an image 48 of the corneal endothelium which is out of focus. When the X-Y alignment is completed and an alignment signal is output from the alignment detecting sensor 4' to the image switching circuit 4'', the images are switched to each other by an image switching signal output from the circuit 4'' as shown in FIG. 31(b). Therefore, according to the embodiment of the invention, the part to be inspected is accurately found out by observing the anterior segment with the monitor 25' as a first step for adjustment without eye estimation as in prior art, and then the corneal endothelium is easily and quickly found out as a second step.

What is claimed is:

1. An apparatus for photographing a corneal endothelium of an eye, comprising:
   an observing optical system for observing the anterior segment of said eye to align optical systems of said apparatus in the up, down, right, and left directions with said eye;
   an illumination optical system for projecting each illumination light emitted by respective light sources for observation and photography onto the cornea of said eye;
   an observing and photographing optical system for observing and photographing the corneal endothelium of said eye by receiving a reflected image from said endothelium, said observing and photographing optical system including an image receiving element for aligning the optical systems of said apparatus by movement in a direction to or from said eye;
   display means for separately displaying respective images of the anterior segment observed immediately before photographing the corneal endothelium of said eye; and
   switching means for switching the display means to display one or the other of the respective images.

2. An apparatus for photographing a corneal endothelium of an eye, comprising:
   an observing optical system for observing the anterior segment of said eye to align optical systems of said apparatus in the up, down, right, and left directions with said eye;
   an illumination optical system for projecting each illumination light emitted by respective light sources for observation and photography onto the cornea of said eye;
   an observing and photographing optical system for observing and photographing the corneal endothelium of said eye by receiving a reflected image from said endothelium, said observing and photographing optical system including an image receiving element for aligning the optical systems of said apparatus for movement in a direction to or from said eye;
   single display means for separately displaying respective images of the anterior segment and the corneal endothelium of said eye simultaneously on the single display means while the corneal endothelium of said eye is observed; and
   switching means for switching the single display means to display one or the other of the respective images.

3. An apparatus for photographing a corneal endothelium of an eye, comprising:
   an illumination optical system for projecting each illumination light emitted by respective light sources for observation and photography onto the cornea of said eye;
   an observing optical system for observing the anterior segment of said eye by receiving an image of said anterior segment on a two-dimensional image receiving element to align optical systems of said apparatus in the X and Y directions with said eye;
   an observing and photographing optical system for observing and photographing the corneal endothelium of said eye by receiving a reflected image from said endothelium on said two-dimensional image receiving element, said observing and photographing optical system including an image receiving element for aligning the optical systems of said apparatus in a Z direction with said eye;
   a displayed-image switching mirror for reflecting said image of the corneal endothelium and guiding said image to said two-dimensional image receiving element when said switching mirror is inserted into the optical path of said anterior segment observing optical system, said mirror being arranged insertable into and removable from said optical path;
   a mirror driving circuit for driving said switching mirror;
   an alignment detecting circuit for detecting alignment signals of the X and Y directions by receiving reflected light from said cornea passing through an optical path diverged from the optical path of said anterior segment observing optical system;
   display means for displaying images of said anterior segment and said endothelium by receiving said images on said two-dimensional image receiving element; and
   displayed-image switching means for controlling said mirror driving circuit to switch a displayed image from said anterior segment to said endothelium and vice versa, said switching means including maintaining means for keeping said switching mirror inserted in the optical path of said anterior segment observing optical system for a given time after completing alignment in the X and Y directions.

4. An apparatus for photographing a corneal endothelium of an eye according to claim 3, wherein a first alignment area in the X and Y directions is presented to said eye, said maintaining means including a circuit corresponding to said first alignment area and a circuit corresponding to a second alignment area in the X and Y directions larger than said first alignment area, said maintaining means an image of the endothelium to be displayed even when an alignment index is located in said second alignment area after switching a displayed image from the anterior segment to the endothelium based on said circuit corresponding to said first area when said alignment index is located in said first area.

5. An apparatus for photographing a corneal endothelium of an eye according to claim 3, wherein said maintaining means is a timer circuit for delaying alignment signals of said X-Y alignment detecting circuit for a given time.

6. An apparatus for photographing a corneal endothelium of an eye according to claim 3, wherein said maintaining means is a hand-operated lock switch for keeping said mirror driving circuit working.

7. An apparatus for photographing a corneal endothelium of an eye according to claim 3, wherein said light source for photography automatically emits illumination light whereas said light source for observation automatically stops emitting illumination light when said displayed-image switching mirror is inserted into said optical path.

* * * * *

UNITED STATES PATENT AND TRADEMARK OFFICE
CERTIFICATE OF CORRECTION

PATENT NO. : 5,381,194
DATED : January 10, 1995
INVENTOR(S) : Kouji NISHIO et al Page 1 of 3

It is certified that error appears in the above-indentified patent and that said Letters Patent is hereby corrected as shown below:

Column 2, Line 20, after "means" insert --are provided--.

Column 2, Line 27, change "objects" to --aspects--.

Column 2, Line 50, change "aspects" to --aspect--.

Column 2, Line 59, change "directions. Illumination" to --directions, illumination--.

Column 3, Line 7, delete ",".

Column 5, Line 32, change "forms" to --form--.

*Column 5, Line 41, change "receving" to --receiving--.

Column 7, Line 22, change "endothelium" to --endothelial--.

Column 7, Line 56, after "of" insert --Fig. 9--.

Column 8, Line 5, change "e" to --E--.

UNITED STATES PATENT AND TRADEMARK OFFICE
CERTIFICATE OF CORRECTION

PATENT NO. : 5,381,194
DATED : January 10, 1995
INVENTOR(S) : Kouji NISHIO et al It is certified that error appears in the above-indentified patent and that said Letters Patent is hereby corrected as shown below:

Column 8, Line 16, change "v" to --V--.

Column 8, Line 30, change "if" to --is--.

Column 8, Line 32, change "focus. The" to --focus, the--.

Column 10, Line 6, change "el" to --el--.

Column 10, Line 21, change "el" to --el--.

UNITED STATES PATENT AND TRADEMARK OFFICE
CERTIFICATE OF CORRECTION

PATENT NO.  : 5,381,194
DATED       : January 10, 1995
INVENTOR(S) : Kouji Nishio et al It is certified that error appears in the above-indentified patent and that said Letters Patent is hereby corrected as shown below:

Column 10, Line 26, change "el" to --el--.

Column 10, Line 41, change "el" to --el--.

Column 11, Line 20, delete "in".

Claim 4, Column 14, Line 47, between "means" and "an", insert --keeping--.

Signed and Sealed this

Twenty-seventh Day of June, 1995

Attest:

BRUCE LEHMAN

*Attesting Officer*  *Commissioner of Patents and Trademarks*